US00PP09193P

United States Patent [19]

Crosby et al.

[11] Patent Number: Plant 9,193

[45] Date of Patent: Jul. 11, 1995

[54] APPLE TREE NAMED *CO-OP 30'*

[75] Inventors: Jeffrey A. Crosby, Louisiana, Mo.; Jules Janick, W. Lafayette, Ind.; Edwin B. Williams, Lafayette, Ind.; Schuyler S. Korban, Champaign, Ind.; Joseph Goffreda, Kendall Park, N.J.; Paul C. Pecknold, W. Lafayette, Ind.

[73] Assignee: Purdue Research Foundation, West Lafayette, Ind.

[21] Appl. No.: 71,239

[22] Filed: Jun. 2, 1993

[51] Int. Cl.[6] ..... A01H 5/00

[52] U.S. Cl. ..... Plt./34.1

[58] Field of Search ..... Plt. 34.1, 35.1

*Primary Examiner*—James R. Feyrer

*Attorney, Agent, or Firm*—Woodard, Emhardt, Naughton, Moriarty & McNett

[57] ABSTRACT

The cultivar of the present invention, designated 'Co-op 30', is a new and distinct cultivar of apple Tree (*Malus*×*domestica* Borkh.). It was discovered in October of 1978 at West Lafayette, Ind., in the course of an attempt to develop improved apple cultivars with high fruit quality and resistance to *Venturia inaequalis* (Cke.) Wint., the causal agent of the scab disease of apple. The tree is a seedling of known parentage planted in May of 1972 in the CL Block of the apple breeding orchard on the old Clark Farm tract of the Purdue Horticulture Research Farm, West Lafayette, Ind. In the above mentioned block, its position was Row 4, Tree 38, having the designation PRI 2693-1 in the breeding records.

2 Drawing Sheets

BACKGROUND OF THE INVENTION

The present new cultivar is designated as also known as Enterprise 'Co-op 30'. It was produced from crossing the seedling PRI 1661-2 as the seed parent and the seedling PRI 1661-1 as the pollen parent in 1971 at West Lafayette, Ind. This sib-mating resulted in 19 seeds, of which eleven survived inoculation with the scab fungus to be planted in field position. 'Co-op 30' was the single selection made from this progeny. This new cultivar carries at least one copy of the genetic factor $V_f$ inherited from *Malus floribunda* Sieb. 821. The $V_f$ factor renders it highly resistant to infection caused by *Venturia inaequalis*. For more than twenty years, trials of apple cultivars containing $V_f$ in every humid production area of the world have shown no breakdown of this resistance. The presence of this factor in 'Co-op 30' has been repeatedly proven by controlled greenhouse inoculation tests of the seedling and fifteen years of observation of the seedling and propagules under natural conditions for infection in the field at the West Lafayette site, and observation of propagules at multiple sites in the United States and abroad for several years. The complete pedigree is shown in the second figure.

The new cultivar produces a moderately vigorous, spreading, round-topped tree. Fruits have a strong tendency to be borne singly on moderate length to long spurs and hangs well on the tree until overripe. 'Co-op 30' is field immune to apple scab. Based on observation in the field, it is highly resistant to fire blight (incited by *Erwinia amylovora* (Burr.) Winslow), resistant to cedar apple rust (incited by *Gymnosporagium juniperi-virginianae* (Schw.)), and moderately resistant to powdery mildew (incited by *Podosphaera leucotricha* (Ell. & Ev.) Salm.).

Flowering occurs in late mid-season, with or after 'Golden Delicious'. The fruit is best suited for use following removal from cold storage in winter and spring. The dessert quality is very good and reaches its peak in December, January, February, and March. Fruit retains characteristic quality (flavor and texture) for 6 months or more in refrigerated storage at 1° C.

After observation, the selection was asexually propagated by grafting on seedling, EMLA-111, and EMLA-7 rootstocks at the above noted Lafayette site. The grafted material has maintained the described characteristics after propagation.

BRIEF DESCRIPTION OF THE FIGURES

The first figure is a photograph showing the leaves and fruit of Co-op 30.

The second figure is a photograph showing the fruit of Co-op 30 on a larger scale.

The third figure, entitled "Pedigree", is a schematic showing the pedigree of Co-op 30.

DETAILED DESCRIPTION OF THE NEW CULTIVAR

The accompanying color photograph shows a typical example of fruit and foliage of 'Co-op 30'. The following is a detailed description of the new cultivar with color designations according to the 1966 Horticultural Colour Chart (Wilson) issued by the Royal Horticultural Society of London.

FLOWERS

Corolla: Average of 48 mm in diameter at anthesis.

Petals: 15 mm×23 mm.

Color: China Rose o24/2 (bud) fading to white tinged with Magenta Rose o27/2 (open flowers).

FRUIT

Shape: Slightly oblate to somewhat truncate. Regular on older trees. May be oblique to lopsided on young trees; length:width ratio=0.91.

Size: Average diameter is 70 to 76 mm.

Color: Undercolor Saffron Yellow (Plate 7/2), overcolor 95% Cardinal Red (Plate 82/2) fading to Orange (Plate 12/1) on light side when shaded.

Skin: Smooth and glossy, moderately tough, medium thick; bloom is scant but fruit becomes waxy after 4 months storage; slightly conspicuous, smooth, round, white dots.

Stem: Short, medium thick.

Cavity: Acute, medium depth, medium width, smooth surface.

Basin: Medium depth, broad breadth, rounded sides, smooth surface.

Calyx: Persistent, partly closed, erect to recurved.

Calyx tube: Urn shaped.

Stamens: Basal.

Core-lines: Meeting.

Core: Median, closed, small.

Carpels: Round, emarginate, smooth.

Seeds: Full compliment, acuminate, non-tufted.

Flesh:

*Texture.*—Medium grained, firm, crisp and breaking at harvest; mellows to firm and crisp after storage.

*Quality.*—Very spicy, rich and spritely acid at harvest; peak quality after one month in storage.

*Color.*—Lighter in hue than Aureolin (Plate 3/3).

Maturity season: October 17 to 25 at West Lafayette, Ind.; two and one half weeks after 'Delicious'.

Keeping quality: Superior; retains quality and texture 6 months or more at 1° C.

Use: Winter dessert apple, appropriate for medium and long term storage.

TREE

Tree: Spreading, round-topped, vigorous, standard bearing habit; fruits borne singly on long spurs, hang well on the tree, even when over-ripe; annual bearing.

Leaves: Ovate; serrate to double serrate margin; apex acute to acuminate, base acute to round; length to width ratio = 1.60. Leaf petioles show slight anthocyanin pigmentation, sometimes intense in at the base.

Pruning/training requirements: Vigorous tree with less than optimum branch angles, may require spreading; canopy will require thinning to provide for adequate light penetration.

Branch angles: Branch angles are 45 to 80 degrees.

Pollination: Requires cross pollination for optimum yield; will not set fruit if emasculated.

Productivity: Moderately productive.

Thinning: Will require thinning to achieve optimum size.

Bark: Current year stems are Garnet Brown (00918/3) on sun-exposed surface, Pea Green (61) on underside of new growth; lenticels on one-year-old wood are raised, about 1 mm in diameter, round, Apricot 609/3; lenticels on 5-year-old trunks are rough, usually linear, about 2 to 3 mm in length.

We claim:

1. A new and distinct apple tree substantially as shown and described, characterized by resistance to apple scab, fire blight, cedar apple rust, and powdery mildew; long storage life; very attractive appearance; very good dessert quality; and maturity approximately two and one half weeks after 'Delicious' and five weeks after 'McIntosh'.

* * * * *

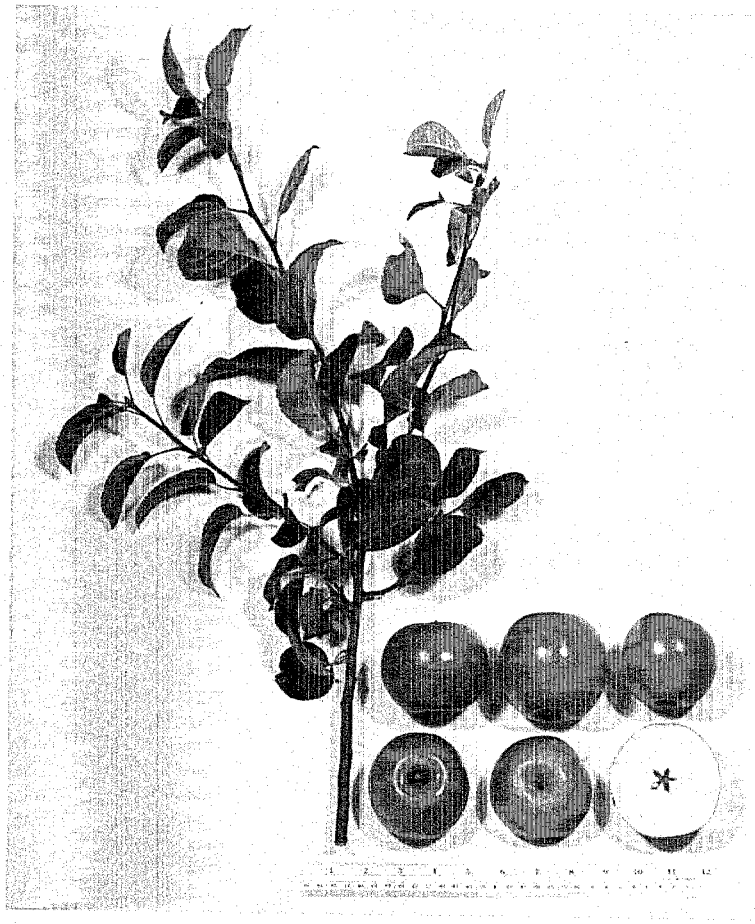
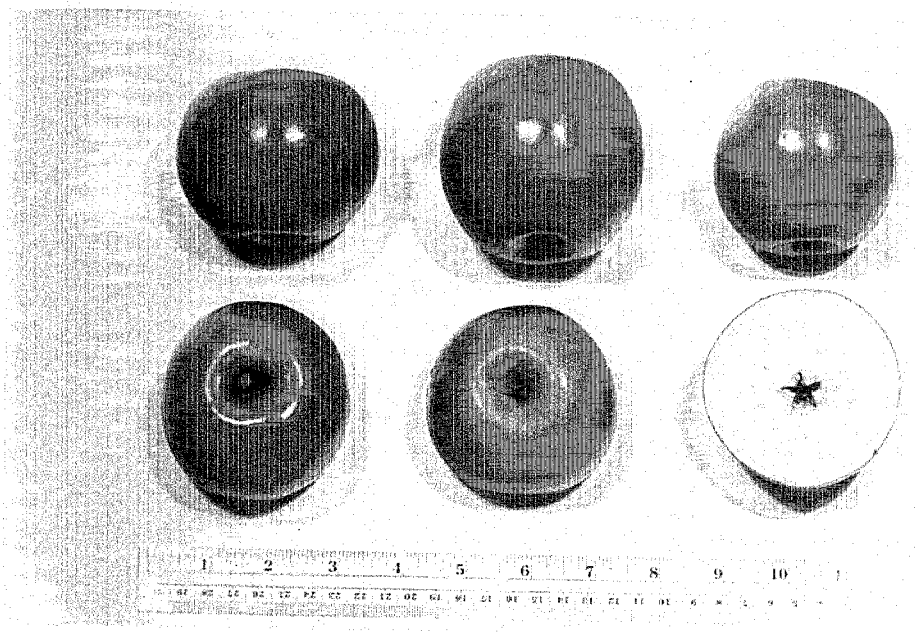
1 2 3 4 5 6 7 8 9 10

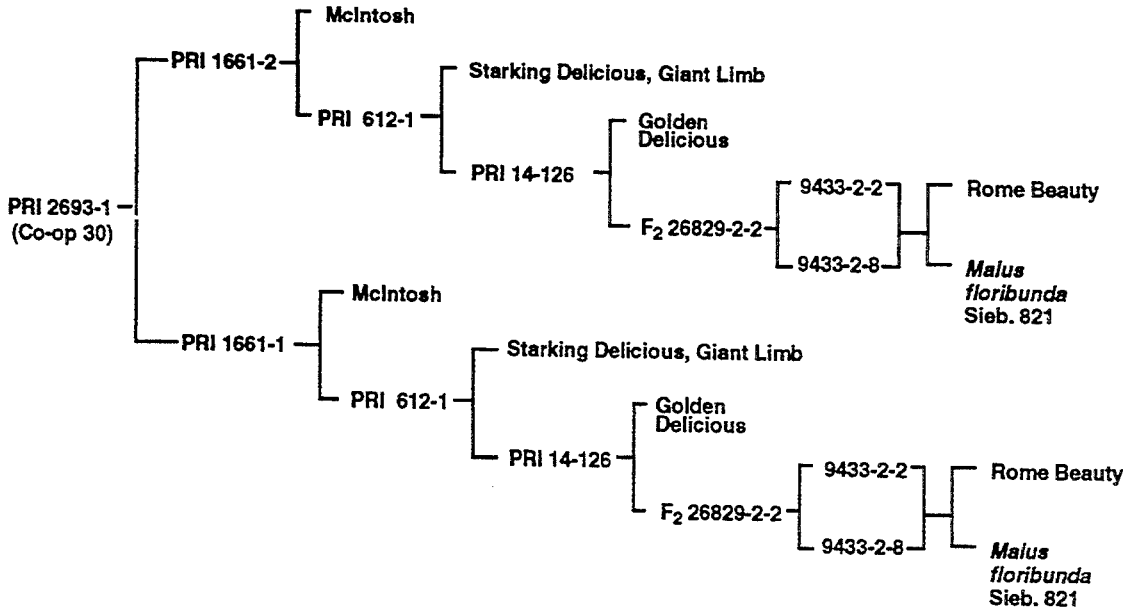
PEDIGREE

UNITED STATES PATENT AND TRADEMARK OFFICE

CERTIFICATE OF CORRECTION

PATENT NO. : PP 09193

DATED : July 11, 1995

INVENTOR(S) : Jeffrey A. Crosby, et al

It is certified that error appears in the above-indentified patent and that said Letters Patent is hereby corrected as shown below:

Column 1, lines 3-4, delete

"also known as Enterprise 'Co-op 30'" and replace it with --'Co-op 30', also known as Enterprise--.

Title page, lines 2-3 of the Abstract, please delete "(Malusxdomestica" and insert in lieu thereof --(Malus Xdomestica--.

Signed and Sealed this

Third Day of October, 1995

*Attest:*

Bruce Lehman

BRUCE LEHMAN

*Attesting Officer*

*Commissioner of Patents and Trademarks*

UNITED STATES PATENT AND TRADEMARK OFFICE

CERTIFICATE OF CORRECTION

PATENT NO. : P 9,193

DATED : July 11, 1995

INVENTOR(S) : Jeffrey A. Crosby, Jules Janick, Edwin B. Williams, Schuyler S. Korban, Joseph Goffreda and Paul C. Pecknold It is certified that error appears in the above-identified patent and that said Letters Patent is hereby corrected as shown below:

On the title page, item [54] and in column 1, line 1:

Please amend the title of this application by inserting --"-- before "CO-OP".

Signed and Sealed this

Fourteenth Day of November, 1995

Bruce Lehman

*Attest:*

BRUCE LEHMAN

*Attesting Officer*

*Commissioner of Patents and Trademarks*